United States Patent
Li et al.

(10) Patent No.: US 10,194,827 B2
(45) Date of Patent: Feb. 5, 2019

(54) ACTIVE PROTECTIVE CIRCUIT FOR A MEASURING AMPLIFIER IN AN ELECTRODE BELT FOR AN ELECTRICAL IMPEDANCE TOMOGRAPH

(71) Applicant: Drägerwerk AG & Co. KGaA, Lübeck (DE)

(72) Inventors: Jianhua Li, Lübeck (DE); Frank Sattler, Lübeck (DE); Karsten Hiltawsky, Stockelsdorf (DE)

(73) Assignee: Drägerk AG & Co. KGaA, Lübeck (DE)

( * ) Notice: Subject to any disclaimer, the term of this patent is extended or adjusted under 35 U.S.C. 154(b) by 106 days.

(21) Appl. No.: 15/372,751

(22) Filed: Dec. 8, 2016

(65) Prior Publication Data

US 2017/0164864 A1 Jun. 15, 2017

(30) Foreign Application Priority Data

Dec. 11, 2015 (DE) .................. 10 2015 016 091

(51) Int. Cl.
  *A61B 5/053* (2006.01)
  *A61B 5/085* (2006.01)
  (Continued)

(52) U.S. Cl.
  CPC ............ *A61B 5/0536* (2013.01); *A61B 5/085* (2013.01); *G01R 27/02* (2013.01);
  (Continued)

(58) Field of Classification Search
  None
  See application file for complete search history.

(56) References Cited

U.S. PATENT DOCUMENTS 3,534,282 A * 10/1970 Day ................... A61B 5/04004
                                                             128/902
3,547,108 A * 12/1970 Seiffert ................ A61B 5/0424
                                                             600/525
(Continued)

FOREIGN PATENT DOCUMENTS

CN        1063942 A      8/1992
CN      102755163 A     10/2012
(Continued)

OTHER PUBLICATIONS

Hang-Ming Yang et al, Performance assessment of active electrode applied in wearable physiological monitoring system, Biomedical and Health Informatics (BHI), 2012 IEEE-EMBS International Conference On, IEEE, Jan. 5, 2012, pp. 472-474.

*Primary Examiner* — Kennedy Schaetzle
(74) *Attorney, Agent, or Firm* — McGlew and Tuttle, P.C.

(57) ABSTRACT

An active protective circuit for a measuring amplifier of an electrical impedance tomograph includes a circuit component arrangement including an electrode input and an output and a control input for a control voltage. The output is configured for connection to a measuring amplifier for an electrical impedance tomograph. The circuit component arrangement creates a conductive connection between the electrode input of the circuit component arrangement and the output of the circuit component arrangement when the applied control voltage is within a first voltage range and does not create a conductive connection when the applied control voltage is within a second voltage range. The voltage being applied to the control input is within the second voltage range when a voltage, which is within a cut-off range, is applied to the electrode input. An electrode belt for impedance tomography has the active protective circuits associated with the electrodes.

19 Claims, 3 Drawing Sheets

(51) Int. Cl.
   *G01R 27/02* (2006.01)
   *H01L 27/02* (2006.01)
   *H03F 1/52* (2006.01)
   *H02H 11/00* (2006.01)

(52) U.S. Cl.
   CPC ...... *H01L 27/0255* (2013.01); *H01L 27/0285* (2013.01); *H02H 11/006* (2013.01); *H03F 1/52* (2013.01); *A61B 2505/01* (2013.01); *A61B 2505/03* (2013.01); *A61B 2560/0266* (2013.01); *A61B 2562/182* (2013.01); *H03F 2200/261* (2013.01)

(56) References Cited

U.S. PATENT DOCUMENTS

| | | | |
|---|---|---|---|
| 4,091,818 A * | 5/1978 | Brownlee | A61N 1/37 607/9 |
| 4,745,923 A * | 5/1988 | Winstrom | A61N 1/37 128/908 |
| 5,196,980 A | 3/1993 | Carson | |
| 5,365,099 A | 11/1994 | Phipps et al. | |
| 5,536,958 A | 7/1996 | Shen et al. | |
| 5,642,252 A | 6/1997 | Sakamoto et al. | |
| 5,647,379 A * | 7/1997 | Meltzer | A61N 1/37 128/897 |
| 5,968,083 A * | 10/1999 | Ciciarelli | A61N 1/08 361/58 |
| 7,511,357 B2 | 3/2009 | Hshieh | |
| 8,032,228 B2 * | 10/2011 | Ameri | A61N 1/056 128/901 |
| 8,965,526 B2 * | 2/2015 | Zhang | A61N 1/3718 607/2 |
| 2003/0144706 A1 * | 7/2003 | Funke | A61N 1/37 607/30 |
| 2007/0049993 A1 * | 3/2007 | Hofmann | A61B 5/0536 607/62 |
| 2008/0258224 A1 | 10/2008 | Hshieh | |
| 2011/0148443 A1 * | 6/2011 | Maktura | A61B 5/0535 324/705 |
| 2014/0100637 A1 * | 4/2014 | Zhang | A61N 1/3718 607/62 |
| 2014/0240036 A1 | 8/2014 | Kurokawa | |
| 2015/0263504 A1 | 9/2015 | Edwards et al. | |
| 2015/0325568 A1 | 11/2015 | Chaudry et al. | |
| 2016/0067511 A1 * | 3/2016 | Rasmussen | A61N 1/3975 607/5 |

FOREIGN PATENT DOCUMENTS

| | | |
|---|---|---|
| DE | 20 2005 013792 U1 | 11/2005 |
| DE | 10 2005 041385 A1 | 3/2007 |
| DE | 10 2008 002330 A1 | 12/2009 |
| EP | 0 848 472 A1 | 6/1998 |
| ES | 2 366 378 T3 | 10/2011 |
| JP | H06 237124 A | 8/1994 |
| JP | 3893429 B2 | 3/2007 |
| WO | 98/49444 A1 | 11/1998 |

* cited by examiner

ACTIVE PROTECTIVE CIRCUIT FOR A MEASURING AMPLIFIER IN AN ELECTRODE BELT FOR AN ELECTRICAL IMPEDANCE TOMOGRAPH

CROSS REFERENCE TO RELATED APPLICATIONS

This application claims the benefit of priority under 35 U.S.C. § 119 of German Application 10 2015 016 091.5 filed Dec. 11, 2015, the entire contents of which are incorporated herein by reference.

FIELD OF THE INVENTION

The present invention pertains to an active protective circuit for a measuring amplifier for an electrical impedance tomograph with a circuit component array as well as an electrode belt for an electrical impedance tomograph with a plurality of electrodes and a plurality of active protective circuits.

BACKGROUND OF THE INVENTION

In electrical impedance tomography, the electric conductivity of a human or animal body between a plurality of electrodes is determined and an optical view of the body is derived from this. A so-called electrode belt with a plurality of electrodes is arranged on the skin surface of the body for measuring the electric conductivity. An alternating current, for example, with a frequency between 10 kHz and 200 kHz, with an amplitude of a few mA, is applied between two electrodes each. The propagation of this alternating current is detected by the remaining electrodes in the form of the drop in voltage between the electrodes and is used as a basis for the calculation of a tomogram in an impedance tomograph. The precise measurement and amplification of the measured voltages requires a highly sensitive electronic unit.

Electrical impedance tomography is nowadays used, among other things, to monitor the lung function of ventilated patients, for example, patients in an intensive care unit. If a cardiac arrest occurs in such patients, a defibrillator is used to reactivate the heart by targeted current pulses. Voltages of up to 5 kV are applied to the patient for a short time in this case. The highly sensitive electronic unit of the electrical impedance tomograph is not configured for such high voltages. Since, however, there is usually also no time for all electrodes to be removed from the patient before the defibrillator is used, other protective measures must be used to protect the electronic unit of the impedance tomograph against the current pulse of the defibrillator. In addition, it is also necessary to automatically disconnect the impedance tomograph from the patient in order to prevent the impedance tomograph from draining too much energy from the current pulse of the defibrillator and the current pulse is possibly no longer strong enough to stop the heart from fibrillating or fluttering.

According to DE 20 2005 013 792 U1, it is known to provide a protective circuit for an EIT apparatus that has a securing mechanism between the electrode on the patient and the signal input at the EIT apparatus. A series connection of two resistors, which is located in front of the first amplifier stage of the EIT apparatus, is inserted into the securing mechanism. Immediately after the beginning of a defibrillation, the electrodes are rapidly separated from the EIT apparatus by means of the securing mechanism. The drawback is that the securing mechanism only functions starting from a certain energy level of the defibrillator pulse and because of its size, this securing mechanism can only be implemented on the EIT apparatus and not on the electrode belt.

An overvoltage protection component, which can be configured as an overvoltage protection lever for a medical apparatus on the body of a patient, is known from DE 10 2008 002 330 A1. In this case, the overvoltage protection component is connected to a medical apparatus having a bipolar interface with a first and a second input. The overvoltage protection component comprises a first and a second capacitor as conversion means, which are arranged downstream at the inputs. Arranged downstream are two Zener diodes, which are connected in series with opposite polarity and electrically connect both input lines. The overvoltage protection component is only provided at the interface at the medical apparatus and not directly on an electrode belt.

A protective circuit for an electrical impedance tomograph is known from DE 10 2005 041 385 A1. This protective circuit, which consists of a series-connected RC circuit with a capacitor and a resistor, together with a spark gap, protects the signal inputs of the impedance tomograph against voltages that are too high during the normal measuring operation. In this connection, the capacitor is used as the actual protection against the actual current pulse. So that the operability of the impedance tomograph is not compromised, the capacitor of the RC circuit must have at least an electric strength of 5 kV. In order to guarantee the electric strength, the capacitor must have a minimal size, which makes the capacitor the component of the protective circuit with the greatest overall installed size. The minimal size of the capacitor leads, however, to it being more or less impossible to implement the protective circuit directly in the electrode belt due to a lack of space. Since actually each of the electrodes of the impedance tomograph must be dually protected, the overall installed size for the protective circuit is further increased.

Since it is more or less impossible to implement the circuit directly in the electrode belt, this circuit is nowadays usually arranged directly in the impedance tomograph. However, all components, from the electrode up to the lines, which lead to the impedance tomograph, must thus have an electric strength of at least 5 kV. In addition, the components must all be configured such that there is no risk due to the defibrillator pulse for medical staff that is in the vicinity of the impedance tomograph. Hence, the components of the electrode belt are relatively complex in terms of manufacture and are expensive. In addition, because of the low voltages that would have to be detected by the electrodes, it would be advantageous to arrange amplifier components directly in the electrode belt. In the current solutions, these active amplifier components would likewise have to have an electric strength of at least 5 kV, so that they are not destroyed by the defibrillator pulse. Since the active amplifier components are otherwise configured to amplify voltages with an amplitude of a few mV or μV, it appears to be very difficult to guarantee an electric strength for a defibrillator pulse at the same time.

SUMMARY OF THE INVENTION

Therefore, among other things, an object of the present invention is to provide an active protective circuit for an impedance tomograph, the size of which is markedly lower than the size of already known protective circuits. The protective circuit is preferably suitable to be inserted directly in an electrode belt for an impedance tomograph and to protect active amplifier components in such an electrode belt.

In a first aspect, the object on which the present invention is based is accomplished by means of an active protective circuit for a measuring amplifier for an electrical impedance tomograph with a circuit component arrangement or circuit component array, wherein the circuit component arrangement has an electrode input and an output and at least one control input for a control voltage. The electrode input of the circuit component arrangement is configured for connection to an electrode of an electrode belt for an electrical impedance tomograph. The output of the circuit component arrangement is configured for connection to a measuring amplifier of an electrical impedance tomograph. The circuit component arrangement is configured such that the circuit component arrangement creates a conductive connection between the electrode input of the circuit component arrangement and the output of the circuit component arrangement when a control voltage being applied to the at least one control input is within a first voltage range. The circuit component arrangement is, furthermore, configured such that the circuit component arrangement does not create a conductive connection between the electrode input of the circuit component arrangement and the output of the circuit component arrangement when the control voltage being applied to the at least one control input is within a second voltage range. The protective circuit includes a control voltage device configured such that the voltage being applied to the at least one control input is within the second voltage range when a voltage, which is within a cut-off range, is applied to the electrode input.

In other words, the active protective circuit according to the present invention comprises a circuit component arrangement, which has at least three active protective circuit inputs: An electrode input, an output (also the applied signal input) and at least one control input for a control voltage. This circuit component arrangement may be arranged, for example, directly in an electrode belt for an impedance tomograph. However, the protective circuit may also be arranged, for example, in the actual impedance tomograph (impedance tomograph device/unit). In any case, the electrode input is, however, configured for connection to an electrode, i.e., the electrode input is electrically connected to an electrode during the operation. Correspondingly, the output of the circuit component arrangement is configured for connection to a measuring amplifier, i.e., the output is electrically connected to a measuring amplifier during the operation. The measuring amplifier may be, for example, a local preamplifier, which is arranged directly in an electrode belt. As an alternative, however, the measuring amplifier may be arranged in the actual impedance tomograph, even if the active protective circuit itself is arranged in the electrode belt.

The circuit component arrangement is configured according to the present invention to operate in two different states. Hence, the circuit component arrangement may have, for example, electronic components that can be operated only in two states, such as, for example, MOSFET (metal oxide semiconductor field effect transistor). This circuit component arrangement is configured such that it conductively connects the electrode input to the output if the control voltage, i.e., the voltage being applied to the control input is within a first voltage range. If the control voltage is within a second voltage range not overlapping with the first voltage range, then the circuit component arrangement does not create a conductive connection between the electrode input of the circuit component arrangement and the output of the circuit component arrangement. In other words, the circuit component arrangement does not forward a signal being applied to the electrode input to the output and thus to the measuring amplifier arranged downstream.

Whether the control voltage is within the first or the second voltage range depends on how high the voltage that is applied to the electrode input is. For example, the protective circuit may, for example, be configured such that the control voltage is permanently within the first voltage range (i.e. continuously within the first voltage range until reset) when the voltage being applied to the electrode input is within a range which is used during the normal measuring operation of the impedance tomograph. The circuit component arrangement then conductively connects the electrode input to the output and forwards the measured voltages directly to the measuring amplifier. If, however, a voltage is applied to the electrode input, which is within a predefined cut-off range, then the control voltage automatically switches to the second range and the connection between the electrode input and the output of the circuit component arrangement is disconnected. Thus, voltages, which are in connection with voltage pulses, which are within the cut-off range, are not forwarded by the circuit component arrangement and thus do not load a measuring amplifier arranged downstream, either. The cut-off range may be defined, for example, by a lower voltage limit, for example, 20 V and be represented as an infinitely open range by this lower voltage limit. However, the cut-off range may have two sections, for example, a first section, which comprises all voltages less than −20 V, and a second section, which comprises all voltages greater than 20 V.

The circuit component arrangement of the active protective circuit is thus advantageously configured such that it disconnects the connection between the electrode input and the output as soon as the voltage being applied to the electrode input switches to a cut-off range, in which the measuring amplifier arranged downstream can no longer be operated with certainty. If, for example, a defibrillator is thus used for resuscitating a patient, on whom an electrode belt for an impedance tomograph with an active protective circuit according to the present invention is placed, then the active protective circuit, more precisely stated, the circuit component arrangement disconnects the connection between the electrode input and the output as soon as the voltage being applied to the electrode input switches to the cut-off range. If the cut-off range is defined as being sufficiently broad, then the circuit component arrangement already disconnects the electrode input at the lower end of the rising edge of the defibrillator pulse and thus prevents a damage to the electronic unit arranged downstream. Since the circuit component arrangement does not have a capacitor that has to receive the actual defibrillator pulse, this circuit component arrangement can be markedly smaller than protective circuits known from the state of the art.

In a preferred embodiment, the output of the circuit component arrangement is connected to the at least one control input of the circuit component arrangement via a blocking component as part of the control voltage device. The blocking component is configured such that the voltage being applied to the output of the circuit component arrangement is only applied to the control input if the voltage being applied to the output of the circuit component arrangement is within the cut-off range.

In other words, there is a connection between the output of the circuit component arrangement and the control input of the circuit component arrangement. This connection comprises at least one electronic component, which is either conductive or non-conductive depending on the voltage being applied to the output of the circuit component arrangement. For example, the component may be a Zener diode (Z diode), which is arranged between the output and the control input such that it blocks during the normal measuring operation and then becomes conductive when the voltage being applied to the output—and thus to the Z diode—switches to the cut-off range. As soon as the blocking component becomes conductive, the voltage being applied to the output of the circuit component arrangement is also applied to the control output. The blocking component and possibly additional components in the connection between the output of the circuit component arrangement and the control input are preferably selected such that the voltage being applied to the control input switches precisely to the second range if the blocking component is conductive and the voltage being applied to the output of the circuit component arrangement switches to the cut-off range. This leads advantageously to the voltage being applied to the output being used directly as a switching threshold in order to switch the circuit component arrangement such that the electrode input is no longer conductively connected to the output.

It is, furthermore, preferred when the active protective circuit, parallel to the circuit component arrangement, has a bypass circuit that connects the input of the circuit component arrangement to the output of the circuit component arrangement. The bypass circuit is configured such that a voltage within the cut-off range is applied to the output of the circuit component arrangement when the circuit component arrangement does not create a conductive connection between the electrode input of the circuit component arrangement and the output of the circuit component arrangement, and the voltage being applied to the input of the circuit component arrangement is within a high-volt range, wherein the high-volt range is a partial range of the cut-off range. The bypass circuit can preferably be formed, for example, by a high-ohmic resistor. The optional bypass circuit advantageously ensures that even if the circuit component arrangement has disconnected the electrode input from the output of the circuit component arrangement, a voltage, which is so high that the control voltage is kept within the second range, is, furthermore, applied to the connection between the output of the circuit component arrangement and the control input, and the connection between the electrode input and the output of the circuit component arrangement remains permanently disconnected (remains disconnected until being reset). However, it has been found that the bypass circuit is not absolutely necessary in order to operate the active protective circuit according to the present invention with certainty.

In a preferred embodiment, the control voltage device of the active protective circuit comprises a memory circuit, which is configured such that a voltage, which is within the second voltage range, is permanently applied (continuously applied until the device is reset) to the at least one control input, when a voltage, which is within the cut-off range, is applied once to the electrode input. In other words, the memory circuit is configured such that in case of the one-time exceeding of the limits of the cut-off range, the voltage being applied to the control input is permanently kept within the voltage range (until there is a reset), in which the circuit component arrangement disconnects the electrode input from the output.

It is, furthermore, preferred when the circuit component arrangement has a first circuit component with an input, an output and a control input. The input of the first circuit component is connected to the electrode input. The output of the first circuit component is connected to the output of the circuit component arrangement. The control input of the first circuit component is connected to the at least one control unit of the circuit component arrangement. The first circuit component is configured such that the circuit component creates a conductive connection between the input of the first circuit component and the output of the first circuit component when a control voltage being applied to the control input of the first circuit component is within the first voltage range, and the first circuit component does not create a conductive connection between the input of the first circuit component and the output of the first circuit component when the control voltage being applied to the control input of the first circuit component is within the second voltage range. The protective circuit is configured such that the voltage being applied to the at least one control unit switches to the second voltage range when a voltage, which exceeds a predefined first threshold value, is applied to the electrode input.

In other words, the circuit component arrangement comprises at least one first circuit component, which has an input, an output and a control input. The input of the first circuit component is connected to the electrode input of the circuit component arrangement, wherein additional components may be arranged between the input of the first circuit component and the electrode input of the circuit component arrangement. The output of the first circuit component is connected to the output of the circuit component arrangement, wherein additional components may also be arranged between the output of the first circuit component and the output of the circuit component arrangement. Finally, the control input of the first circuit component is connected to the at least one control input of the circuit component arrangement. The first circuit component is configured such that the first circuit component disconnects the input of the first circuit component and the output of the first circuit component from one another when the control voltage being applied to the control input of the first circuit component is within the second voltage range, and electrically connects them with one another when the control voltage being applied to the control input of the first circuit component is within the first voltage range. In this case, the circuit component arrangement and thus also the first circuit component are configured such that the switch from the first to the second voltage range occurs in the first circuit component precisely if the voltage being applied to the electrode input exceeds a predefined first threshold value. In other words, the first circuit component is configured to disconnect the connection between the electrode input of the circuit component arrangement and the output of the circuit component arrangement precisely if the voltage being applied to the electrode input exceeds a positive threshold value. This positive threshold value cannot, for example, be identical to a lower limit of an upwards open section of the cut-off range.

The first circuit component is preferably a normally off n-channel MOSFET with a drain terminal, a source terminal and a gate terminal. The drain terminal forms the input of the first circuit component, the source terminal forms the output of the first circuit component, and the gate terminal forms the control input of the first circuit component. The first circuit component is thus only conductive if a positive control voltage is applied to the gate terminal of the n-channel MOSFET. If no or a negative control voltage is applied to the gate terminal, then the n-channel MOSFET blocks. The use of a normally off n-channel MOSFET is preferred since the active protective circuit becomes fail-safe as a result of this, i.e., the protective circuit protects a measuring amplifier arranged downstream even if it is not directly supplied with a control voltage, i.e., it is itself not active.

In a preferred embodiment, the output of the first circuit component is connected to the control input of the first circuit component via the blocking component, wherein the blocking component is configured such that the voltage being applied to the output of the first circuit component is applied to the control input of the first circuit component only if the voltage being applied to the output of the first circuit component is within the cut-off range. The blocking component is formed by two series-connected Z diodes, wherein each Z diode has a conducting direction and a blocking direction and wherein the two series-connected Z diodes are interconnected such that the conducting direction of the one Z diode corresponds to the blocking direction of the other Z diode. The use of two Z diodes, which are suitably selected and connected head-to-tail, has, on the one hand, the advantage that the one Z diode prevents the voltage supply arranged permanently at the control input of the first circuit component from also being applied to the output of the first circuit component and thus to the measuring amplifier arranged downstream. On the other hand, it is, however, also ensured that the voltage being applied to the control input switches to the second range when the voltage being applied to the output of the first circuit component switches to the cut-off range or exceeds the predefined first threshold value.

It is, furthermore, preferred when the active protective circuit, parallel to the circuit component arrangement, optionally has the bypass circuit which connects the input of the circuit component arrangement to the output of the first circuit component, wherein the circuit component arrangement is configured such that a voltage within the cut-off range is applied to the output of the first circuit component when the first circuit component does not create a conductive connection between the input of the circuit component arrangement to the output of the first circuit component, and the voltage being applied to the input of the circuit component arrangement is within the high-volt range. The bypass circuit has at least one high-ohmic resistor. This embodiment of the bypass circuit offers the already described advantages of a bypass circuit.

As an alternative, it is preferred when the memory circuit is configured such that a voltage, which is within the second voltage range, is continuously applied to the control input of the first circuit component when a voltage, which is within the cut-off range, is once applied to the electrode input. The memory circuit is formed by a flip-flop. The memory circuit preferably comprises an active component in the form of a flip-flop, which can adopt two states and switches between the two states when it receives a signal at a trigger input. Depending on in which of the two states the flip-flop is, a different voltage is applied to a control output of the flip-flop.

For example, the memory circuit is configured such that, in a first state, a voltage provided by the memory circuit is not applied to the control input of the first circuit component and, in a second state, a voltage is applied to the control input of the first circuit component, which leads to the resulting voltage being applied to a control input of the first circuit component being within the second voltage range. The first circuit component thus disconnects the connection between the input of the first circuit component and the output of the first circuit component and thus also the connection between the electrode input of the circuit component arrangement and the output of the circuit component arrangement. In this case, the trigger input, for example, can be connected to the output of the first circuit component and be configured such that a signal that leads to the switch between the two states is a voltage pulse, which is within the cut-off range. Thus, the flip-flop would precisely switch its state if the connection between the electrode input of the circuit component arrangement and the output of the circuit component arrangement shall be disconnected. The use of a memory circuit in the form of a flip-flop has the advantage that, for example, the restarting of an electrode belt, in which the active protective circuit is installed, is prevented after the electrode belt has been exposed to a defibrillator pulse once. Erroneous measurements by the impedance tomograph are prevented from being made in the case of damage possibly generated by the defibrillator pulse or the impedance tomograph is likewise prevented from being damaged due to a damaged circuit. It is, however, preferred, when, for example, a switch is provided, with which the flip-flop can be restored to the first state again, after the integrity of the active protective circuit and of the remaining components of the electrode belt have been checked and no defects were found.

In a preferred embodiment, the circuit component arrangement comprises at least two control inputs and a second circuit component with an input, an output and a control input. A first control input of the at least two control inputs is connected to the control input of the first circuit component. The input of the second circuit component is connected to the electrode input of the circuit component arrangement. The output of the second circuit component is connected to the output of the circuit component arrangement. The control input of the second circuit component is connected to a second control input of the at least two control inputs of the circuit component arrangement. The first and the second circuit components are connected in series. The second circuit component is configured such that the second circuit component creates a conductive connection between the input of the second circuit component and the output of the second circuit component when a control voltage being applied to the control input of the second circuit component is within a third voltage range and the second circuit component does not create a conductive connection between the input of the second circuit component and the output of the second circuit component when the voltage being applied to the control input of the second circuit component is within a fourth voltage range. The circuit component arrangement is configured such that the voltage being applied to the at least one control input switches to the fourth voltage range when a voltage, which falls below a predefined second threshold value, is applied to the electrode input.

In other words, the active protective circuit in this preferred embodiment comprises, besides the first circuit component, a second circuit component. The two circuit components are connected in series, i.e., the input of the one circuit component is connected to the output of the other circuit component. For example, the input of the second circuit component may be connected to the electrode input, the output of the second circuit component is connected to the input of the first circuit component, and the output of the first circuit component is connected to the output of the circuit component arrangement. The second circuit component is thus arranged between the first circuit component and the electrode input. The second circuit component is configured such that it creates a conductive connection between the input of the second circuit component and the output of the second circuit component when the voltage being applied to the control input of the second circuit component is within a third range and disconnects the input of the second circuit component from the output of the second circuit component when the control voltage is within a fourth range. The first voltage range may be identical, for example, to the third voltage range; however, it is also possible that the first voltage range is, for example, between +5 V and +10 V and the third voltage range is between −10 V and −5 V. The second voltage range could also be identical to the fourth voltage range. It is, however, also conceivable that the second voltage range comprises all voltages less than 5 V and the fourth voltage range comprises all voltages greater than −5 V. In any case, the circuit component arrangement is configured such that the voltage being applied to the control input of the second circuit component switches to the fourth voltage range, i.e., the second circuit component is not conductive any longer, when a voltage, which falls below a predefined second threshold value, is applied to the electrode input. The predefined second threshold value may be the upper limit, for example, for a second section of the cut-off range. It is advantageously ensured by the use of such a second circuit component that the active protective circuit cuts off both in case of negative voltage pulses and in case of positive voltage pulses.

In this connection, it is preferred when the second circuit component is a normally off p-channel MOSFET with a drain connection, a source connection and a gate terminal. The drain terminal forms the input of the second circuit component, the source terminal forms the output of the second circuit component, and the gate terminal forms the control input of the second circuit component. The use of a normally off p-channel MOSFET has the advantage that it is not conductive in case of positive control voltages. Besides, the use of a p-channel MOSFET has the same advantages as the use of an n-channel MOSFET as a first circuit component. By combining a first circuit component in the form of an n-channel MOSFET with a second circuit component in the form of a p-channel MOSFET, it is ensured that the active protective circuit reliably disconnects the connection between the electrode and the measuring amplifier arranged downstream even in case of a bipolar defibrillator pulse.

In a second aspect, the object on which the present invention is based is accomplished by an electrode belt for an electrical impedance tomograph with a plurality of electrodes and a plurality of protective circuits according to one of the above embodiments. At least one protective circuit is associated with each electrode and each active protective circuit is associated with only one electrode. The electrode input of the circuit component arrangement of each active protective circuit is connected to the electrode, with which the active protective circuit is associated. The advantages of the electrode belt according to the present invention correspond to the advantages of the embodiments of the active protective circuits that are used in the electrode belt according to the present invention.

The present invention will be explained in detail below on the basis of drawings, which show various exemplary embodiments of active protective circuits and an exemplary embodiment of an electrode belt according to the present invention The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Referring to the drawings, identically designated components are provided with identical reference numbers in the following description of the exemplary active protective circuit embodiments from FIGS. 1 through 5.

Figure 1:
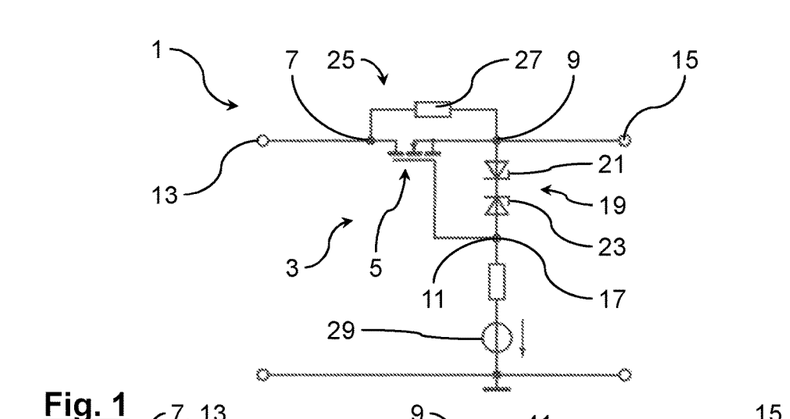
FIG. 1 is a view showing a first exemplary embodiment of an active protective circuit according to the present invention.

FIG. 1 shows a first exemplary embodiment of an active protective circuit 1 according to the present invention with a circuit component arrangement or circuit component arrangement 3. The circuit component arrangement 3 comprises a first circuit component (conductive connection circuit component) 5 in the form of a normally off n-channel MOSFET 5. The n-channel MOSFET 5 has a drain terminal 7, which at the same time forms the input 7 of the first circuit component 5. Furthermore, the n-channel MOSFET 5 has a source terminal 9, which forms the output 9 of the first circuit component 5. Finally, the n-channel MOSFET 5 also comprises a gate terminal 11, which forms the control input 11 of the first circuit component 5.

The input 7 of the first circuit component 5 is connected to the electrode input 13 of the circuit component arrangement 3. The electrode input 13 is suitable for connection to an electrode of an electrode belt for an electrical impedance tomograph. The output 9 of the first circuit component 5 is connected to the output 15 of the circuit component arrangement 3. The output 9 is suitable for connection to a measuring amplifier of an electrical impedance tomograph. The measuring amplifier may be arranged, for example, together with the active protective circuit 1 in the electrode belt. This has the advantage that the voltages detected by the electrode connected to the electrode input can be locally amplified in the electrode belt and the transmission of the measurement signal to the impedance tomograph is less prone to error and even smaller voltages can be transmitted. However, the active protective circuit 1 may be arranged in the electrode belt and the measuring amplifier is arranged in the actual impedance tomograph. The control input 11 of the first circuit component 5 forms at the same time the first control input 17 of the circuit component arrangement 3.

The active protective circuit 1 shown in FIG. 1 further comprises a control voltage device comprising a blocking component 19 with two Z (Zener) diodes 21, 23 connected head-to-tail. The blocking component 19 connects the output 9 of the first circuit component 5 to the control input 11 of the first circuit component 5. As is known, the two Z diodes 21, 23 have each a blocking direction and a conducting direction, wherein a first Z diode 21 of the two Z diodes 21, 23 is connected such that its conducting direction is opposite the conducting direction of a second Z diode 23 of the two Z diodes 21, 23.

Furthermore, the active protective circuit 1 comprises a bypass circuit 25, which is formed by a high-ohmic resistor. The bypass circuit 25 connects the input 7 of the first circuit component 5 to the output 9 of the first circuit component 5. Finally, the control voltage device also comprises a voltage source 29, via which an operating voltage of, for example, 5 V can be applied to the control input 11 of the first circuit component 5. The voltage source 29 is connected to ground at one end and may be provided, for example, in the form of a battery or be fed directly from an impedance tomograph.

The active protective circuit 1 comprises a first circuit component 5 in the form of a normally off n-channel MOSFET 5. By using the normally off n-channel MOSFET 5, the active protective circuit 1 is advantageously fail-safe, since the electrode input 13 is disconnected from the output 15 of the circuit component arrangement 3 when the active protective circuit 1 is not energized.

If an operating voltage within a first voltage range is applied via the voltage source 29 of the control voltage device (control voltage regulation circuit arrangement) to the control input 11, during the normal measuring operation, then the first circuit component 5 provides a conductive connection between the input 7 of the first circuit component and the output 9 of the first circuit component. The electrode input 13 is thus also conductively connected to the output 15 of the circuit component arrangement 3 and measurement signals possibly received by the electrode are forwarded to a measuring amplifier arranged downstream. Conversely, currents applied (applied signals) to the active protective circuit 1 via the output 15, which are needed for the operation of the electrical impedance tomograph device, are forwarded to the electrode input as well for feeding the electrodes (feeding the applied signals). The first Z diode 21 prevents the operating voltage provided by the voltage source 29 from being applied to the output 9 of the first circuit component 5 and prevents the forwarded measurement signal from being falsified. The two Z diodes 21, 23, series-connected head-to-tail, limit, in addition, the gate-source voltage of the MOSFET 5 in both directions.

The control voltage arrangement of the active protective circuit 1 is configured such that when a voltage is applied to the electrode input 13 and thus also to the output 9 of the first circuit component 5, which lies within a cut-off range, more precisely, is above a predefined threshold value, the control voltage being applied to the control input 11 of the first circuit component 5 is no longer sufficient to conductively connect the first circuit component 5. The first circuit component 5 then disconnects the connection between the input 7 and the output 9. It is ensured by using the second Z diode 23 that the voltage, which is applied between the output 9 of the first circuit component and the control input 11, is limited to a maximum value. Thus, the measuring amplifier, which is arranged downstream of the active protective circuit 1, is protected against a voltage pulse being applied to the electrode input 13.

It is advantageously ensured by using the bypass circuit 25 that a sufficiently high voltage is still applied to the output 9 even after the disconnection of the conductive connection between the input 7 and the output 9 of the first circuit component 5, so that the first circuit component 5 continues to keep the connection disconnected as long as the voltage being applied to the electrode input 13 is within a high-volt range. If the voltage drops so low that the second Z diode 23 is no longer conductive and the voltage difference between the control input 11 of the circuit component 5 and the output 9 thereof switches to the first voltage range again, then the voltage being applied by the voltage source 29 to the control input 11 of the first circuit component 5 is sufficient to conductively connect the circuit component 5. I.e., the circuit component again connects the input 7 of the first circuit component 5 conductively to the output 9 of the first circuit component 5.

Figure 2:
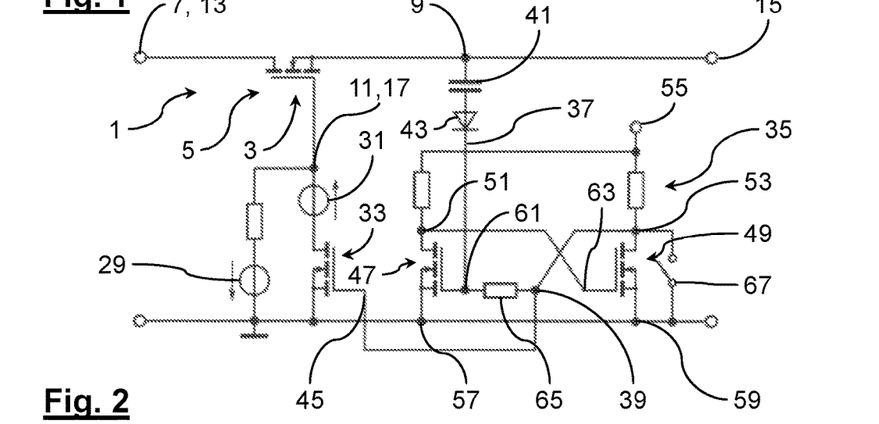
FIG. 2 is a view showing a second exemplary embodiment of an active protective circuit according to the present invention.

FIG. 2 shows a second exemplary embodiment of an active protective circuit 1 according to the present invention with a circuit component arrangement 3, which comprises a first circuit component 5 in the form of a normally off n-channel MOSFET 5. As in the first exemplary embodiment shown in FIG. 1, the n-channel MOSFET 5 has a drain terminal 7, which forms the input 7 of the first circuit component 5 and is connected to the electrode input 13 of the circuit component arrangement 3. Furthermore, the n-channel MOSFET 5 comprises a source terminal 9, which forms the output 9 of the first circuit component 5 and is connected to the output 15 of the circuit component arrangement 3. Finally, the n-channel MOSFET 5 also comprises a gate terminal 11, which forms the control input 11 of the first circuit component 5 and at the same time the first control input 17 of the circuit component arrangement 3. Analogously to the first exemplary embodiment, the active protective circuit 1 in FIG. 2 comprises a voltage source 29, via which a control voltage within the first voltage range can be applied to the control input 11 of the first control component 5. The voltage source 29 is connected to ground at one end.

The second exemplary embodiment of a protective circuit 1 according to the present invention comprises, in addition, a second voltage source 31, which is likewise connected to the control input 11 of the first circuit component 5. The second voltage source 31 is connected to ground via a circuit component 33 in the form of a normally off n-channel MOSFET 33, i.e., the second voltage source 31 is only active if the n-channel MOSFET 33 is conductive. In this case, both the voltage source 29 and the second voltage source 31 are applied to the control input 11 of the first circuit component 5. The voltage provided by the second voltage source 31 is selected such that the sum of the voltages provided by the two voltage sources 29, 31 is within the second voltage range, in which the first circuit component 5 does not create a conductive connection between the input 7 and the output 9 of the first circuit component 5 and thus between the electrode input 13 and the output 15 of the circuit component arrangement 3, either.

The control of the circuit component 33 is carried out by means of a memory circuit 35 in the form of a flip-flop 35. The memory circuit 35 comprises a trigger input 37 and a circuit output 39. The trigger input 37 is connected to the output 9 of the first circuit component 5 via a capacitor 41 and a diode 43; the circuit output 39 is connected to a gate terminal 45 of the n-channel MOSFET 33, which forms the circuit component 33. The memory circuit 35 is configured such that a voltage within a second voltage range, in which the n-channel MOSFET 33 is not conductive and the second voltage source 31 is thus not active, is applied to the circuit output 39 and thus to the gate terminal 45 of the circuit component 33 as well, when the active protective circuit 1 is operated during the normal measuring operation. The memory circuit 35 is then in a first state. If the memory circuit 35 receives a trigger pulse at the trigger input 37, which may be, for example, in the rising edge of a voltage pulse of a defibrillator, which is within the cut-off range, then the memory circuit 35 switches from the first state to a second state, in which a voltage within a second voltage range, in which the circuit component 33 is conductive and the second voltage source 31 is connected to ground and is thus active, is applied to the circuit output 39 and thus to the gate terminal 45 of the circuit component 33. In this case, the first circuit component 5 disconnects the connection between the input 7 and the output 9 of the first circuit component 5. Components of an impedance tomograph arranged downstream of the output 15 of the circuit component arrangement 3 are thus protected against possible voltage pulses. The memory circuit 35 advantageously prevents the circuit component arrangement 3 from being able to be restarted without actions being taken after a voltage pulse within a cut-off range is applied once.

The actual memory circuit 35 comprises a first memory circuit component 47 and a second memory circuit component 49. The two memory circuit components 47, 49 are formed by a normally off n-channel MOSFET 47, 49. Both memory circuit components 47, 49 have a drain terminal 51, 53, which are each connected to an operating voltage source 55. Furthermore, each of the memory circuit components 47, 49 has a source terminal 57, 59, which are grounded. The ground may be formed, for example, by the ground of the impedance tomograph. Finally, each of the memory circuit components 47, 49 also has a gate terminal 61, 63. The gate terminal 61 of the first memory circuit component 47 is connected to the drain terminal 53 of the second memory circuit 49 via a resistor 65. The gate terminal 63 of the second memory circuit component 49 is connected directly to the drain terminal 51 of the first memory circuit component 47. The trigger input 37 and the circuit output 39 are both connected between the gate terminal 61 of the first memory circuit component 47 and the drain terminal 53 of the second memory circuit component 49, wherein the trigger input 37 is arranged directly on the gate terminal 61 of the first memory circuit component 47 and the resistor 65 is arranged between the trigger input 37 and the circuit output 39.

If the active protective circuit 1, which is shown in FIG. 2, is started, then first the second memory circuit component 49 is connected conductively, while the first memory circuit component 47 is not conductive. Thus, the voltage provided by the operating voltage source 55 at the drain terminal 53 of the second memory circuit component 49 drops to ground directly via the second memory circuit component 49. Thus, a sufficiently high voltage is not applied to the circuit output 39 in order to connect the circuit component 33 conductively. If a trigger signal is received via the trigger input 37, then the first memory circuit component 47 is connected conductively and a sufficiently high voltage is no longer applied to the gate terminal 63 of the second memory circuit component 49 in order to continue to keep this second memory circuit component 49 conductive. Hence, the second memory circuit component 49 blocks the connection between the drain terminal 53 and the source terminal 59. This leads to the voltage at the gate terminal 61 of the first memory circuit component 47 increasing to the extent that the first memory circuit component 47 is kept conductive. At the same time, a sufficiently high voltage is applied to the circuit output 39 and thus also to the gate terminal 45 of the circuit component 33 in order to connect the circuit component 33 conductively. The first circuit component 5 thus switches to a second state, in which the connection between the input 7 and the output 9 of the first circuit component 5 is disconnected. Thus, the active protective circuit 1 is advantageously prevented from being restarted after it has been deactivated once because of an overvoltage.

A switch 67 is provided in order to continue to use the active protective circuit 1, however, after the operability of the active protective circuit 1 and of the components arranged downstream as well as of the electrode arranged upstream has been checked. If the switch 67 is closed, the voltage being applied to the drain terminal 53 of the second memory circuit component 49 drops directly to ground. Thus, a sufficiently high voltage is no longer available at the gate terminal 61 of the first memory circuit component 47 to keep the first memory circuit component 47 conductive. However, the voltage at the gate terminal 63 of the second memory circuit component 49 thus increases again to the extent that the second memory circuit component 49 is connected conductively again and the memory circuit 35 switches to the first state again. In the first state, a sufficiently high voltage is not applied to the circuit output 39 to connect the circuit component 33 conductively. Thus, the voltage being applied to the control input 11 of the first circuit component 5 is within the first range again and the first circuit component 5 creates a conductive connection between the input 7 and the output 9 of the first circuit component 5. The switch 67 thus advantageously makes it possible to reset the memory circuit 35.

Figure 3:
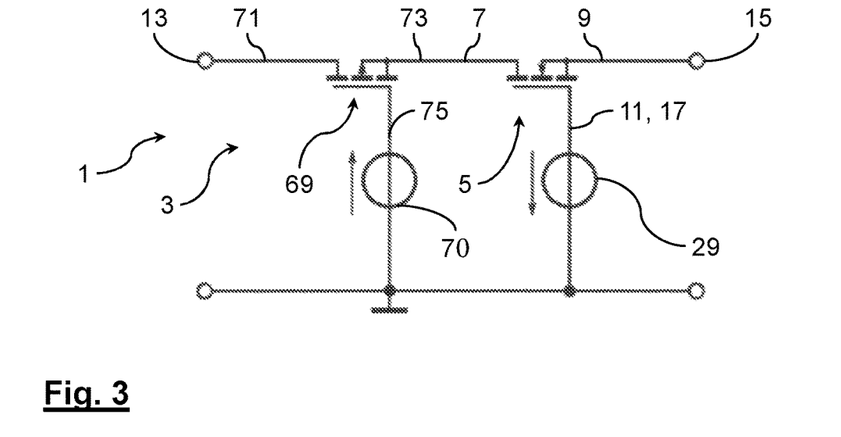
FIG. 3 is a view showing a third exemplary embodiment of an active protective circuit according to the present invention.

A third exemplary embodiment of an active protective circuit 1 is schematically shown in FIG. 3. This circuit illustrates only that a protection against bipolar voltage pulses, which are applied to an electrode input 13, can be achieved by means of a circuit component arrangement 3 with a series connection of a first circuit component 5 in the form of a normally off n-channel MOSFET 5 and of a second circuit component 69 in the form of a normally off p-channel MOSFET 69. The second circuit component 69 likewise has an input 71, an output 73 and a control input 75. The input 71 of the second circuit component 69 is formed by the drain terminal 71 of the p-channel MOSFET 69. The output 73 of the second circuit component 69 is formed by the source terminal 73 of the p-channel MOSFET 69. The control input 75 of the second circuit component 69, which is at the same time a second control input 75 of the circuit component arrangement 3, is formed by the gate terminal 75 of the p-channel MOSFET 69. In addition, the active protective circuit 1 has another voltage source 70, via which an operating voltage within a third range, in which the second circuit component 69 is conductive, can be applied to the second control input 75.

The configuration of the first circuit component 5 corresponds to the one that was already described in detail in reference to the exemplary embodiments shown in FIGS. 1 and 2. The embodiment of an active protective circuit 1 shown in FIG. 3 has the advantage that it disconnects the connection between the electrode input 13 and the output 15 of the circuit component arrangement 3 both in case of a negative voltage pulse at the electrode input 13 and in case of a positive voltage pulse at the electrode input 13. In this connection, the second circuit component 69 is configured such that it disconnects the connection between the input 71 of the circuit component 69 and the output 73 of the circuit component 69 when the voltage being applied to the electrode input 13 falls below a second predefined threshold value, while the first circuit component 5 is configured such that it disconnects the connection between the input 7 and the output 9 of the first circuit component 5 when the voltage being applied to the electrode input 13 exceeds a first predefined threshold value.

Figure 4:
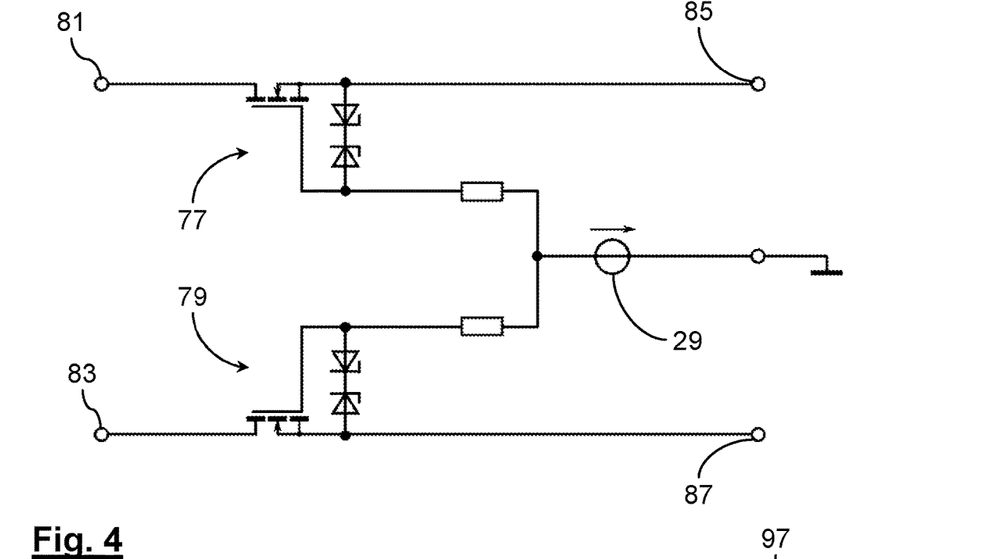
FIG. 4 is a view showing a first exemplary embodiment of two active protective circuits according to the present invention interconnected with one another.

FIG. 4 shows an interconnection of two active protective circuits 77, 79, as it appears during the operation of an electrical impedance tomograph. Two electrode inputs 81, 83 are always combined with one another during the operation of an electrical impedance tomograph in order to feed a current or to measure the voltage that drops between these two electrode inputs 81, 83. The two active protective circuit correspond to the active protective circuits 1, which is shown in FIG. 1. Therefore, the details of the protective circuits 77, 79 will not be dealt with further here. The protective circuits 77, 79 differ from the active protective circuit 1 shown in FIG. 1 only in that a bypass circuit 25 has been dispensed with, since this bypass circuit is not absolutely necessary. Both protective circuits 77, 79 are operated via a common voltage source 29, which is provided, for example, directly by the impedance tomograph and which is connected to the ground of the impedance tomograph device.

FIG. 4 does not show that the outputs 85, 87 in the impedance tomograph are connected to one another via a conductive connection. In order to prevent the defibrillator pulse from being able to propagate through the electrode input 81, 83 and the outputs 85, 87 into the measuring amplifier arranged downstream and the impedance tomograph arranged downstream, it is hence sufficient when one of the two active protective circuits 77, 79 disconnects the connection between the electrode input 81, 83 associated with it and the output 85, 87 associated with it.

Figure 5:
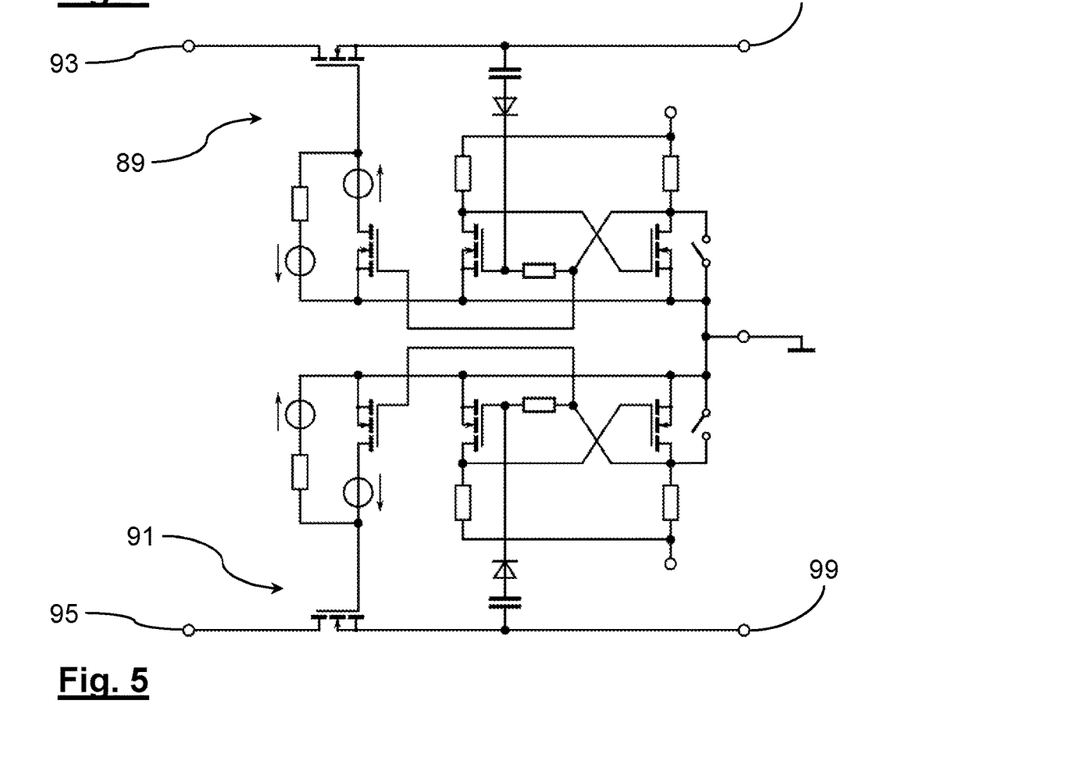
FIG. 5 is a view showing a second exemplary embodiment of two active protective circuits according to the present invention interconnected with one another.

Analogously to the embodiment in FIG. 4, FIG. 5 shows a combination of two active protective circuits 89, 91, in which the protective circuits 89, 91 correspond to the exemplary embodiment shown in detail in FIG. 2. Therefore, a detailed description of the circuits will also be dispensed with here. As in FIG. 4, the two electrodes connected to the electrode inputs 93, 95 are connected conductively via the outputs 97, 99 within the impedance tomograph, for example, via a measuring amplifier. The two connected electrodes are arranged on the patient at different locations and are on different potentials in case of a defibrillator pulse. Hence, it is in turn sufficient that when a defibrillator pulse is applied to a patient, on whom the electrodes connected to the electrode inputs 93, 94 are placed, one of the two protective circuits 89, 91 disconnects the connection between the respective electrode input 93, 95 and the respective output 97, 99 in order to protect the electronic components arranged downstream of the active protective circuits 89, 91 against the defibrillator pulse and in order to prevent too much energy of the defibrillator pulse from flowing into the impedance tomograph. Since a positive voltage pulse is also applied to one of the two electrode inputs 93, 95 in case of a bipolar defibrillator pulse, one of the two active protective circuit 89, 91 will in any case disconnect the connection between the associated electrode input 93, 95 and the associated output 97, 99. The arrangements shown in FIGS. 4 and 5 are thus advantageously protected even without the use of a series connection consisting of an n-channel MOSFET and a p-channel MOSFET in case of bipolar defibrillator pulses.

Figure 6:
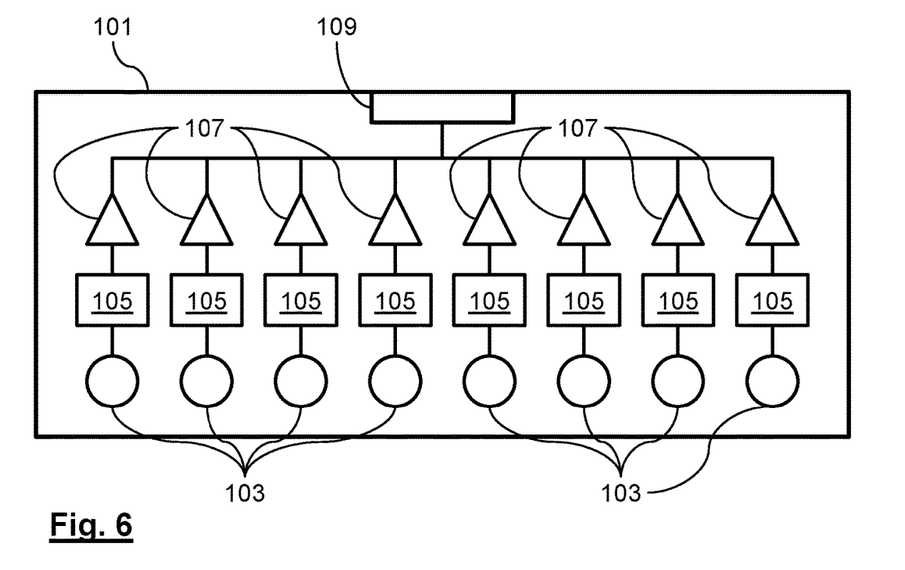
FIG. 6 is a schematic view of an exemplary embodiment of an electrode belt according to the present invention.

Finally, FIG. 6 shows a schematic view of an exemplary embodiment of an electrode belt 101 according to the present invention for an electrical impedance tomograph. The electrode belt 101 comprises a plurality of electrodes 103, which are intended for arrangement on the skin of a patient. Each of the electrodes 103 is connected to an active measuring amplifier 107 via an active protective circuit 105 according to the present invention, which measuring amplifier is likewise arranged on the electrode belt 101. The active protective circuits 105 may be protective circuits according to one of the above exemplary embodiments. In this case, the electrode inputs of the active protective circuits 105 are each connected to the electrodes and the outputs are connected to the active measuring amplifiers 107 arranged downstream. Each active measuring amplifier 107 is connected to an output 109, via which the electrodes 103 can finally be connected to the actual impedance tomograph. The advantages of the electrode belt 101 correspond to the advantages of the active protective circuits 105 used therein. In addition, the arrangement of the active measuring amplifier 107 directly in the electrode belt 101 makes possible an active amplification of the measured voltage near the electrode 103, with which the sensitivity of the impedance tomograph can be increased against a one-time amplification in the actual impedance tomograph.

While specific embodiments of the invention have been shown and described in detail to illustrate the application of the principles of the invention, it will be understood that the invention may be embodied otherwise without departing from such principles.

APPENDIX

List of Reference Numbers

1 Active protective circuit
3 Circuit component arrangement
5 First circuit component, n-channel MOSFET
7 Input of the first circuit component, drain terminal of the n-channel MOSFET
9 Output of the first circuit component, source terminal of the n-channel MOSFET
11 Control input of the first circuit component, gate terminal of the n-channel MOSFET
13 Electrode input
15 Output of the circuit component arrangement
17 First control input of the circuit component arrangement
19 Blocking component
21 Z diode
23 Z diode
25 Bypass circuit
27 High-ohmic resistor
29 Voltage source
31 Second voltage source
33 Circuit component, n-channel MOSFET
35 Memory circuit, flip-flop
37 Trigger input
39 Circuit output
41 Capacitor
43 Diode
45 Gate terminal of the circuit component 33
47 First memory circuit component
49 Second memory circuit component
51 Drain terminal of the first memory circuit component
53 Drain terminal of the second memory circuit component
55 Operating voltage source
57 Source terminal of the first memory circuit component
59 Source terminal of the second memory circuit component
61 Gate terminal of the first memory circuit component
63 Gate terminal of the second memory circuit component
65 Resistor
67 Switch
69 Second circuit component, p-channel MOSFET 70 Voltage source
71 Input of the second circuit component, drain terminal of the p-channel MOSFET
73 Output of the second circuit component, source terminal of the p-channel MOSFET
75 Second control input of the circuit component arrangement, control input of the second circuit component, gate terminal of the p-channel at the MOSFET
77 Active protective circuit
79 Active protective circuit
81 Electrode input
83 Electrode input
85 Output
87 Output
89 Active protective circuit
91 Active protective circuit
93 Electrode input
95 Electrode input
97 Output
99 Output
101 Electrode belt
103 Electrode
105 Active protective circuit
107 Measuring amplifier
109 Output of the electrode belt

What is claimed is:

1. An electrical impedance tomograph measuring amplifier active protective circuit comprising:
 a circuit component arrangement comprising:
  an electrode input configured for connection to an electrode of an electrode belt for an electrical impedance tomograph;
  an output configured for connection to a measuring amplifier of an electrical impedance tomograph;
  at least one control input for a control voltage; and
  at least one conductive connection circuit component configured to create a conductive connection between the electrode input and the output when the control voltage, applied to the control input, is within a first voltage range and to not create a conductive connection between the electrode input and the output when the control voltage, applied to the at least one control input, is within a second voltage range; and
 at least one control voltage regulation circuit configured such that the control voltage, applied to the control input, is within the second voltage range when a voltage, within a cut-off range, is applied to the electrode input, the control voltage regulation circuit comprising a blocking component connecting the output to the at least one control input, wherein the blocking component is configured such that the voltage applied to the output is only applied to the control input if the voltage being applied to the output is within the cut-off range.

2. An active protective circuit in accordance with claim 1, further comprising a bypass circuit parallel to the circuit component arrangement, the bypass circuit connecting the input of the circuit component arrangement to the output of the circuit component arrangement, wherein the bypass circuit is configured such that a voltage within the cut-off range is applied to the output of the circuit component arrangement when the circuit component arrangement does not create a conductive connection between the electrode input of the circuit component arrangement and the output of the circuit component arrangement, and the voltage being applied to the electrode input of the circuit component arrangement is within a high-volt range, wherein the high-volt range is a partial range of the cut-off range.

3. An active protective circuit in accordance with claim 1, wherein the control voltage regulation circuit comprises a memory circuit configured such that a voltage, which is within the second voltage range, is continuously applied to the at least one control input when a voltage, which is within the cut-off range, is applied once to the electrode input.

4. An active protective circuit in accordance with claim 1, wherein the cut-off range is defined by a lower voltage limit between 40 V and 10 V.

5. An active protective circuit in accordance with claim 1, wherein the cut-off range is defined by a lower voltage limit of about 20 V.

6. An active protective circuit in accordance with claim 1, wherein the cut-off range has two sections, wherein a first section comprises all voltages less than −10 V and a second section comprises all voltages greater than 10 V.

7. An active protective circuit in accordance with claim 1, wherein the cut-off range has two sections, wherein a first section comprises all voltages less than −20 V, and a second section comprises all voltages greater than 20 V.

8. An electrical impedance tomograph measuring amplifier active protective circuit, comprising:
 a circuit component arrangement comprising:
  an electrode input configured for connection to an electrode of an electrode belt for an electrical impedance tomograph;
  an output configured for connection to a measuring amplifier of an electrical impedance tomograph;
  at least one control input for a control voltage; and
  at least one conductive connection circuit component configured to create a conductive connection between the electrode input and the output when the control voltage, applied to the control input, is within a first voltage range and to not create a conductive connection between the electrode input and the output when the control voltage, applied to the at least one control input, is within a second voltage range; and
 at least one control voltage regulation circuit configured such that the control voltage, applied to the control input, is within the second voltage range when a voltage, within a cut-off range, is applied to the electrode input, wherein:
  the at least one conductive connection circuit component comprises a component input connected to the electrode input, a component output connected to the output of the circuit component arrangement and a control input connected to the at least one control input of the circuit component arrangement;
  the at least one conductive connection circuit component is configured to provide a conductive connection between the component input and the component output, when the control voltage is within the first voltage range and to not provide a conductive connection between the component input and the component output when the control voltage is within the second voltage range; and
  the at least one control voltage regulation circuit is configured such that the control applied to the at least one control input switches to the second voltage range when a voltage, which exceeds a predefined first threshold value, is applied to the electrode input.

9. An active protective circuit in accordance with claim 8, wherein:

the at least one conductive connection circuit component comprises a normally off n-channel MOSFET with a drain terminal, a source terminal and a gate terminal;

the drain terminal forms the component input, the source terminal forms the component output and the gate terminal forms the component control input.

10. An active protective circuit in accordance with claim 8, wherein:

the control voltage regulation circuit comprises a blocking component connecting the output to the at least one control input, wherein the blocking component is configured such that the voltage applied to the output is only applied to the control input if the voltage being applied to the output is within the cut-off range;

the component output is connected to the component control input via the blocking component;

the blocking component is configured such that the voltage being applied to the component output is only applied to the component control input if the voltage being applied to component output is within the cut-off range;

the blocking component comprises two series-connected Z diodes, wherein each Z diode has a conducting direction and a blocking direction, and wherein the two series-connected Z diodes are interconnected such that the conducting direction of one of the Z diodes corresponds to the blocking direction of another of the Z diodes.

11. An active protective circuit in accordance with claim 10, further comprising a bypass circuit parallel to the circuit component arrangement, the bypass circuit connecting the input of the circuit component arrangement to the output of the circuit component arrangement, wherein:

the circuit component arrangement is configured such that a voltage within the cut-off range is applied to component output does not create a conductive connection between the electrode input and the component output, and the voltage being applied to the electrode input is within the high-volt range; and the bypass circuit has at least one high-ohmic resistor.

12. An active protective circuit in accordance with claim 8, wherein:

the control voltage regulation circuit comprises a memory circuit configured such that a voltage, which is within the second voltage range, is continuously applied to the at least one control input when a voltage, which is within the cut-off range, is applied once to the electrode input; and the memory circuit is formed by a flip-flop.

13. An active protective circuit in accordance with claim 8, wherein:

the at least one conductive connection circuit component is a first component and the component input is a first component input, the component output is a first component output and the component control input is a first control input;

the circuit component arrangement further comprises at least a second control input and at least a second conductive connection circuit component with a second component input, a second component output and a second component control input;

the second component input is connected to the electrode input, the second component output is connected to the output of the circuit component arrangement, and the second component control input of the second circuit component is connected to the second control input;

the first circuit components and the second circuit component are connected in series with the component input connected to the second component output;

the second circuit component is configured to provide a conductive connection between the second component input and the second component output when the control voltage applied to the second component control input is within a third voltage range, and to not provide a conductive connection between the second component input and the second component output when the control voltage applied to the second component control input is within a fourth voltage range;

the control voltage regulation circuit is configured such that the voltage applied to the second component control input switches to the fourth voltage range when a voltage, which falls below a predefined second threshold value, is applied to the electrode input.

14. An active protective circuit in accordance with claim 13, wherein:

the second circuit component comprises a p-channel MOSFET with a drain terminal, a source terminal and a gate terminal; and the drain terminal forms the second component input, the source terminal forms the second component output, and the gate terminal forms the second component control input.

15. An electrical impedance tomograph electrode belt comprising:

a plurality of electrodes;

a plurality of active protective circuits, wherein at least one active protective circuit is associated with each electrode, and each active protective circuit is associated with only one electrode, wherein each active protective circuit comprises:

a circuit component arrangement comprising:

an electrode input configured for connection to an electrode of an electrode belt for an electrical impedance tomograph;

an output configured for connection to a measuring amplifier of an electrical impedance tomograph;

at least one control input for a control voltage;

at least one conductive connection circuit component configured to create a conductive connection between the electrode input and the output when the control voltage, applied to the control input, is within a first voltage range and to not create a conductive connection between the electrode input and the output when the control voltage, applied to the at least one control input, is within a second voltage range; and at least one control voltage regulation circuit configured such that the control voltage, applied to the control input, is within the second voltage range when a voltage, within a cut-off range, is applied to the electrode input, wherein the electrode input of the circuit component arrangement of each active protective circuit is connected to the respective electrode with which the active protective circuit is associated.

16. An electrode belt in accordance with claim 15, wherein the control voltage regulation circuit comprises a blocking component connecting the output to the at least one control input, wherein the blocking component is configured such that the voltage applied to the output is only applied to the control input if the voltage being applied to the output is within the cut-off range.

17. An electrode belt in accordance with claim 16, further comprising a bypass circuit parallel to the circuit component arrangement, the bypass circuit connecting the input of the circuit component arrangement to the output of the circuit component arrangement, wherein the bypass circuit is configured such that a voltage within the cut-off range is applied to the output of the circuit component arrangement when the circuit component arrangement does not create a conductive connection between the electrode input of the circuit component arrangement and the output of the circuit component arrangement, and the voltage being applied to the electrode input of the circuit component arrangement is within a high-volt range, wherein the high-volt range is a partial range of the cut-off range.

18. An electrode belt in accordance with claim 15, wherein the control voltage regulation circuit comprises a memory circuit configured such that a voltage, which is within the second voltage range, is continuously applied to the at least one control input when a voltage, which is within the cut-off range, is applied once to the electrode input.

19. An electrode belt in accordance with claim 15, wherein:

the at least one conductive connection circuit component comprises a component input connected to the electrode input, a component output connected to the output of the circuit component arrangement and a control input connected to the at least one control input of the circuit component arrangement;

the at least one conductive connection circuit component is configured to provide a conductive connection between the component input and the component output, when the control voltage is within the first voltage range and to not provide a conductive connection between the component input and the component output when the control voltage is within the second voltage range; and the at least one control voltage regulation circuit is configured such that the control applied to the at least one control input switches to the second voltage range when a voltage, which exceeds a predefined first threshold value, is applied to the electrode input.

* * * * *